(12) United States Patent
Pekarske et al.

(10) Patent No.: US 10,290,371 B1
(45) Date of Patent: May 14, 2019

(54) SYSTEM OF MEDICAL DEVICES AND METHOD OF CONTROLLING THE SAME

(71) Applicant: General Electric Company, Shenectady, NY (US)

(72) Inventors: Matthew Richard Pekarske, Grafton, WI (US); Bruce Friedman, Jasper, GA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/883,942

(22) Filed: Jan. 30, 2018

(51) Int. Cl.
*G16H 40/40* (2018.01)
*A61B 5/00* (2006.01)
*G16H 40/63* (2018.01)

(52) U.S. Cl.
CPC .......... *G16H 40/40* (2018.01); *A61B 5/0026* (2013.01); *G16H 40/63* (2018.01); *A61B 5/0006* (2013.01); *A61B 5/0008* (2013.01)

(58) Field of Classification Search
None
See application file for complete search history.

(56) References Cited

U.S. PATENT DOCUMENTS

| | | | |
|---|---|---|---|
| 6,112,224 A * | 8/2000 | Peifer | G06F 19/3418 709/202 |
| 6,434,258 B2 | 8/2002 | Wiens | |
| 8,018,584 B1 | 9/2011 | Amir | |
| 8,139,945 B1 | 3/2012 | Amir et al. | |
| 8,310,364 B2 | 11/2012 | Derks et al. | |
| 8,514,071 B2 | 8/2013 | Derks et al. | |
| 8,620,682 B2 | 12/2013 | Bechtel et al. | |
| 8,633,806 B2 | 1/2014 | Amir | |
| 9,055,928 B2 | 6/2015 | McCombie et al. | |
| 9,219,984 B1 | 12/2015 | Amir | |
| 9,306,665 B1 | 4/2016 | Amir | |

(Continued)

OTHER PUBLICATIONS

Gorges, Mattias et al., "Improving Alarm Performance in the Medical Intensive Care Unit Using Delays and Clinical Context", International Anesthesia Research Society, vol. 108, No. 5, May 2009.

(Continued)

*Primary Examiner* — Curtis J King
(74) *Attorney, Agent, or Firm* — Andrus Intellectual Property Law, LLP

(57) ABSTRACT

A medical device system includes a first patient monitor having a proximity beacon that communicates compatibility information and a medical device associated with the same patient as the first patient monitor. The medical device includes a device proximity detector that detects a proximity beacon when the first patient monitor is within a predetermined proximity range of the medical device, and a device workflow module executable on a processor to receive compatibility information and determine whether the first patient monitor is a compatible device. If so, then a direct communication channel is established with the first patient monitor and a device workflow is identified that corresponds with a monitor workflow executable by the first patient monitor. The medical device then communicates with the first patient monitor via the direct communication channel to execute the identified device workflow until a termination condition is reached.

21 Claims, 4 Drawing Sheets

(56) References Cited

U.S. PATENT DOCUMENTS

| | | | |
|---|---|---|---|
| 9,341,700 B2 | 5/2016 | Amir et al. | |
| 2007/0001837 A1* | 1/2007 | Larson | G06K 19/0723 340/539.1 |
| 2008/0140157 A1* | 6/2008 | Goetz | A61N 1/37235 607/59 |
| 2010/0313105 A1* | 12/2010 | Nekoomaram | G06F 8/654 714/807 |
| 2012/0172687 A1* | 7/2012 | Wood | G06F 8/60 600/323 |
| 2012/0323090 A1* | 12/2012 | Bechtel | A61B 5/6889 600/306 |
| 2012/0323591 A1* | 12/2012 | Bechtel | G06F 19/321 705/2 |
| 2012/0323592 A1* | 12/2012 | Bechtel | G06F 19/3456 705/2 |
| 2013/0268890 A1* | 10/2013 | Jensen | G06Q 10/20 715/825 |
| 2013/0346108 A1* | 12/2013 | Kamen | G16H 40/63 705/3 |
| 2014/0055233 A1* | 2/2014 | Vetrivel | G07C 11/00 340/5.8 |
| 2014/0145848 A1 | 5/2014 | Amir | |
| 2014/0180711 A1* | 6/2014 | Kamen | G06Q 10/06 705/2 |
| 2014/0185805 A1* | 7/2014 | Andersen | H04W 12/02 380/270 |
| 2015/0019250 A1* | 1/2015 | Goodman | H04N 21/4227 705/2 |
| 2015/0155912 A1* | 6/2015 | Winward | A61B 5/0215 375/257 |
| 2015/0182694 A1* | 7/2015 | Rosinko | A61M 5/14244 604/151 |
| 2015/0199487 A1* | 7/2015 | Grauds | A61L 2/10 235/375 |
| 2015/0370973 A1* | 12/2015 | Jones | G06F 19/325 705/2 |
| 2017/0185953 A1* | 6/2017 | Dalforno | G06Q 10/087 |

OTHER PUBLICATIONS

Janssen, Brian D., unpublished U.S. Appl. No. 15/497,867, filed Apr. 26, 2017.

Janssen, Brian D., unpublished U.S. Appl. No. 15/497,936, filed Apr. 26, 2017.

* cited by examiner

SYSTEM OF MEDICAL DEVICES AND METHOD OF CONTROLLING THE SAME

BACKGROUND

The present disclosure generally relates to medical device systems and methods that provide patient monitoring and/or treatment delivery or other care to patients, and more specifically to medical device systems and methods including medical devices that detect proximity of other medical devices and/or non-medical devices associated with the patient and communicate to execute coordinated work flows.

In the field of medicine, patients are often connected to or associated with multiple separate medical devices at one time, each providing respective patient monitoring and/or treatment delivery and care functions. Oftentimes, such monitoring of multiple physiological characteristics involves the use of several monitoring devices simultaneously, such as a pulse oximeter, a blood pressure monitor, a cardiac monitor, a temperature monitor, etc. These monitoring devices may be separate devices or elements within a larger multifunction patient monitoring device. Additional monitoring, treatment, and/or support devices and systems may further be connected to or associated with the patient, such as for delivering fluids, medication, anesthesia, respiration assistance, etc. Each of these devices and systems have their own functions in the overall patient care, and each may generate one or more alarms to alert a clinician of a problem, which may be a problem with the patient's physiology or health status, or maybe a technical problem with the monitoring and/or treatment delivery device.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a medical device system includes a first patient monitor having a proximity beacon that communicates compatibility information and a medical device associated with the same patient as the first patient monitor. The medical device includes a device proximity detector that detects a proximity beacon when the first patient monitor is within a predetermined proximity range of the medical device, and a device workflow module executable on a processor to receive compatibility information and determine whether the first patient monitor is a compatible device. For compatible devices, a direct communication channel is established with the first patient monitor and a device workflow is identified that corresponds with a monitor workflow executable by the first patient monitor. The medical device then communicates with the first patient monitor via the direct communication channel to execute the identified device workflow until a termination condition is reached.

One embodiment of a method of controlling a system of medical devices connected to a patient includes, in a first patient monitor monitoring a physiological parameter of the patient, detecting with a device proximity detector that a medical device is within a proximity range of the first patient monitor. Compatibility information is received from the medical device, and a determination is made on whether the medical device is compatible with the first patient monitor. If so, then a direct communication channel is established with the patient monitor. The patient monitor communicates with the medical device via the direct communication channel to identify one of a set of available monitor workflows that corresponds with one of a set of available device workflows executable by the medical device. At least one termination condition is established for the identified monitor workflow. The patient monitor then communicates with the medical device via the direct communication channel so as to execute the identified monitor workflow until the termination condition is reached.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present inventor has recognized that currently available medical devices for providing patient care, such as bed-side devices for patient monitoring, drug delivery, environmental and temperature regulation, physical therapy devices, or the like, are discreet devices that perform their tasks without an awareness or communication between one another. Thus, clinicians are required to manually interact with multiple devices when providing care for their patients. Clinician interaction with multiple devices provides an added burden on clinicians, slows down patient care, and introduces human error. In view of his recognition of the foregoing issues and problems in the relevant art, the inventor has developed the disclosed medical device systems and methods that provide automatic recognition and workflow communication between devices, thereby facilitating clinical interaction between medical devices attached to a particular patient. This provides opportunity for streamlining and reducing clinician interaction with the various devices, provides more accurate and immediate device control, streamlines device tasks in order to reduce power consumption, streamlines information sharing, reduces false alarms, and enhances patient care reporting capabilities. Thereby, the safety and effectiveness of patient care is improved.

Figure 1:
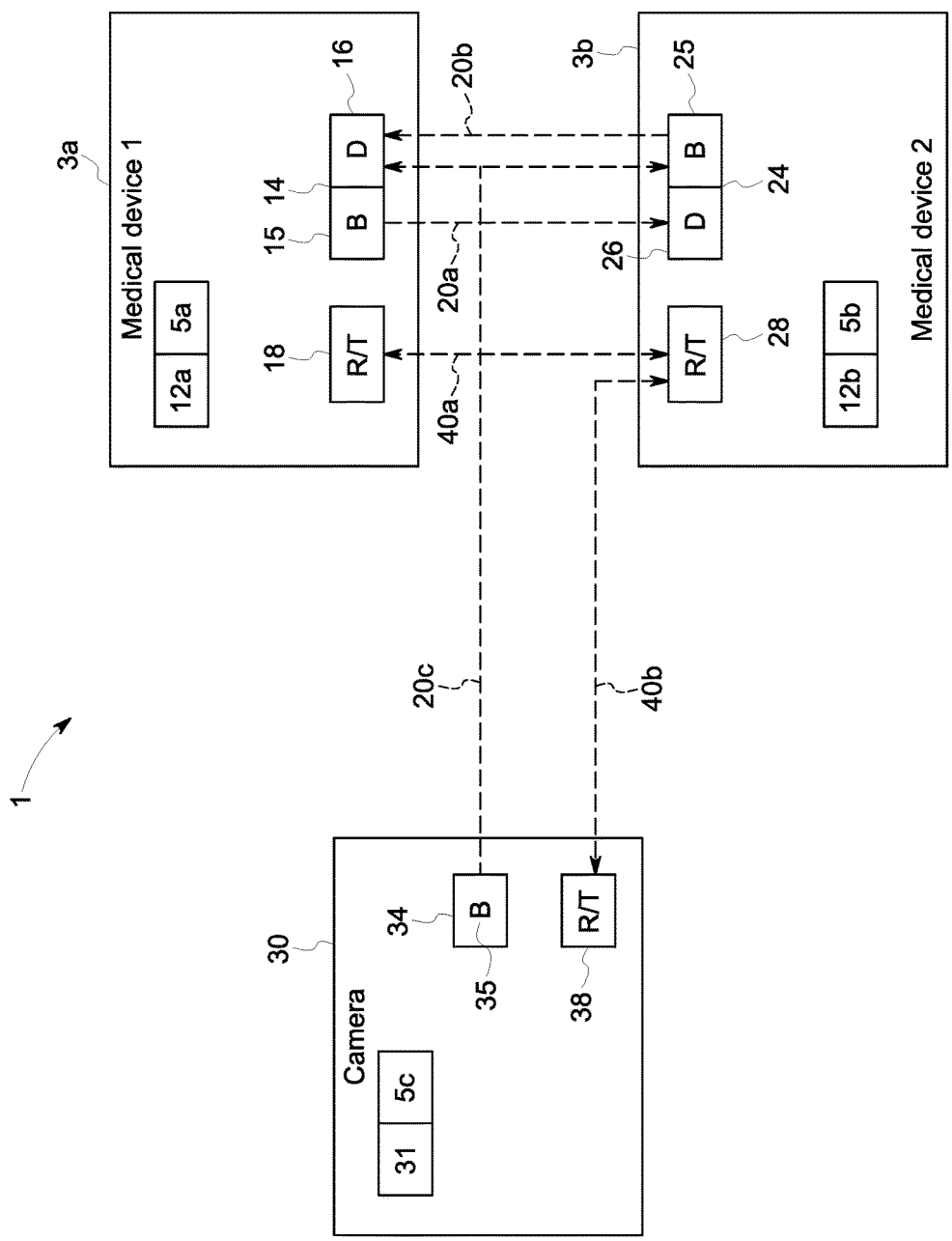
FIG. 1 is a schematic diagram of an exemplary medical device system according to the present disclosure.

FIG. 1 is a schematic diagram depicting an exemplary embodiment of a medical device system 1. The medical devices 3 included in the system 1 automatically detect one another and exchange compatibility information to assess their respective compatibility with one another. The medical devices 3a and 3b further compare workflow capabilities to determine whether they each contain corresponding work flows that could be mutually executed to provide synergy between the medical devices 3a and 3b and/or automate or improve their respective functions. Various exemplary workflows for different exemplary medical devices 3a and 3b are described throughout. To provide just a few initial examples, workflows between a drug delivery device and a patient monitor may correlate drug delivery rate and changes in physiological conditions, to 1) adjust alarm limits to avoid false alarms due to drug-induced changes, and 2) control drug delivery based on the measured physiological parameter data to facilitate achievement of desired effects in the monitored patient physiology.

The system 1 may further include non-medical devices, such as a camera, an audio recording device, and/or a patient communication device facilitating remote communication between a clinician and the patient and/or with an individual co-located with the patient. To provide just one example, the system 1 may include a camera 30 that communicates with a patient monitor such that, when an alarm limit is crossed, the camera 30 is controlled to video record the patient to facilitate immediate remote observation by a remotely located clinician.

Specifically, FIG. 1 depicts a two medical devices 3a, 3b, each having a proximity communication system 14, 24 that includes a proximity beacon 15, 35 that communicates, or broadcasts, compatibility information for a predefined range (e.g. at a predefined power level). The proximity communication system 14, 24 further includes a proximity detector 16, 26 that detects proximity beacon signals 20 from other medical devices 3a, 3b such that the beacons can be received at the proximity detector 16, 26. Accordingly, the compatibility information regarding the respective devices is exchanged when the medical devices 3a and 3b are within a predetermined distance from one another. Any of multiple proximity-based sensor technologies can be utilized by the proximity communication systems 14, 24, examples of which include near field communication (NFC), radio frequency identification (RFID), Bluetooth, iBeacon, or the like. Moreover, various proximity-based technologies may be employed in a single implementation of a medical device system 1, where various medical devices may require different ranges of detection based on their respective available workflows and/or expected interactions with other medical devices 3a, 3b in the system. Thus, in certain examples, a particular medical device 3a, 3b may have multiple proximity communication systems imbedded therein, enabling various types of proximity-based technologies and communication with various types of other medical devices 3a, 3b at various distance ranges.

Thereby, each medical device 3a, 3b continually communicates, or broadcasts, compatibility information so that it can be discovered and/or its presence verified by other devices 3a, 3b, 30 within the system. Likewise, each medical device 3a, 3b may continually look for proximity beacons from other devices in the system. Compatibility information may be any information that allows a receiving device to assess compatibility with the broadcasting device. In certain examples, compatibility information may include a device type generally describing the medical device or other device (e.g., patient monitor, ECG monitor, video camera, or infusion pump), a make and/or model of the device, a serial number of the device, and/or any other information that may enable compatibility assessment by other devices in the system. Alternatively or additionally, the compatibility information may include information identifying the patient to which the medical device 3a, 3b or other device is paired, such as a patient identifier, a case number, etc. Determination of compatibility by a device receiving compatibility information may include comparing the received compatibility information with criteria stored in a compatibility database. For example, each medical device 3a, 3b may have stored locally, or otherwise have access to, a database of information identifying compatible devices, such as compatible device types, makes and models, serial numbers, and/or other identifying information that can be used to compare compatibility information from other devices in order to identify compatible devices. Additionally, compatibility may require receipt of a patient identifier that matches the patient identification number for current operation of the inquiring medical device, thereby the respective medical device 3a, 3b can be assured not to pair with a medical device or other device for a different patient, such as another patient located very close to the patient monitored by the respective medical device 3a, 3b.

In certain embodiments, the compatibility database may further include a list of already-discovered compatible devices and/or a list of already-discovered incompatible devices. Namely, once a device has been identified as either compatible or incompatible, that information may be stored in the compatibility database in order to expedite future compatibility assessments. For example, the medical device 3a, 3b may first check the list of compatible and incompatible devices within the compatibility database before conducting a more detailed analysis of whether the compatibility information sufficiently matches compatibility criteria.

Each device within the medical device system 1 may further include a workflow control module 5, which is a software application executable on a processor in the device to manage compatibility workflow assessments. Referring to the example of 51, the first medical device 3a contains a first workflow control module 5a executable on a first processor 12a therein. Likewise, the second medical device 3b contains its own workflow control module 5b executable on its own processor 12b. Similarly, other devices within the system may also contain their own workflow control modules managing the compatibility assessments and/or workflows executed thereby.

In the example of FIG. 1, the system 1 contains a camera 30 having its own workflow control module 5c executable on the processor 31 of the camera device 30. The camera has its own proximity communication system 34 which in the depicted embodiment only includes a proximity beacon 35 broadcasting compatibility information regarding the camera 30. In such an embodiment, the camera 30 does not detect other devices in the system and is passive in the initial identification and compatibility assessment process. In other embodiments, the camera 30 or other device in the system may have an active proximity communication system 34 that includes a proximity detector 36 in addition to the proximity beacon 35.

In the depicted example, the proximity beacon 15 of the first medical device 3a emits beacon signal 20a, which is received at the proximity detector 26 of the second medical device 3b. Similarly, the proximity beacon 25 of the second medical device 3b emits beacon signal 20b that is received by the proximity detector 16 in the first medical device. The proximity beacon 35 of the camera is received by both the proximity detectors 16, 26 of the medical devices 3a, 3b.

Each respective workflow control module 5 manages, in addition to the compatibility assessment, establishing a direct communication channel and a workflow assessment with compatible devices. A workflow is a sequence of steps and/or set of actions that the respective device 3a, 3b, 30 is capable of executing in coordination with a compatible device within the system 1. Once compatibility has been established, the compatible devices 3a, 3b, 30 establish a direct communication channel to exchange workflow information and/or to exchange information as part of executing the workflows. The direct communication channel may be established according to any known communication means and protocol, including but not limited to Ethernet, Wi-Fi, wireless medical telemetry service (WMTS), Bluetooth, ZigBee, or similar. In other embodiments, the direct communication channel could utilize the proximity-based technology, and thus where minimal amounts of data are transmitted to assess and carry out workflows, such direct communication functions may be carried out using the hardware for the proximity communication systems 14, 24, 34.

In the embodiment of FIG. 1, each device 3a, 3b, 30 includes a respective direct communication receiver/transmitter 18, 28, 38 configured to transmit and receive information via the common protocol established between the devices. The receiver/transmitters 18, 28, 38 may include separate receiving and transmitting devices, or may include an integrated device providing both receiving and transmitting functions, such as a transceiver. Receiver/transmitter 18 in the first medical device 3a communicates with the receiver/transmitter 28 in the second medical device 3b via direct communication channel 40a. Similarly, the receiver/transmitter 28 in the second medical device 3b communicates with the receiver/transmitter 38 in the camera 30 via the direct communication channel 40b. Accordingly, the second medical device 3b has established two direct communication links 40a and 40b, one for each compatible device 3a and 30. As illustrated, every device 3a, 3b, 30 in the system 1 may not be compatible with every other device 3a, 3b, 30 in the system 1. In the illustrated example, the second medical device 3b is compatible with, and thus has established direct communication channels with, both the first medical device 3a and the camera 30. The first medical device 3a is only compatible, and has established a direct communication channel 40a, with the second medical device 3b.

The assessment and designation of available workflows may account for the current monitoring and/or care needs of the patient, as well as the capability of each respective device 3a, 3b, 3c within the system. For example, the workflow control module 5 may query a workflow database 43, which may be stored locally on the respective device or otherwise is accessible to the respective device, to determine the available device workflows based on the current operating conditions of the respective device 3a, 3b, 30. Each compatible device communicates its available device workflows to the compatible device 3a, 3b, 30 and receives the available device workflows for the compatible device, as well. Thus, referring to the depicted example in FIG. 2, the hub 13 (being the central communicator for the patient monitor 3a) may communicate its available monitor workflows utilizing the sensing devices 4a, 4b to the treatment delivery device 3b, and the treatment delivery device 3b may communicate its available treatment delivery workflows to the patient monitor 3a.

Each workflow control module 5a, 5b assesses the device workflows for the compatible device as compared to its own workflows to determine whether there is any correspondence between the two workflow lists. For example, a drug delivery medical device that delivers medication to regulate heart rate may seek heart rate information from a patient monitor. If the patient monitor has a device workflow that delivers heart rate information, then the workflows may be determined to correspond, and a match identified. This workflow could be used to determine if the infusion had the desired effect on the heart rate as well as prevent spurious heart rate alarms. To provide another example, two patient monitoring devices may cooperate to provide reliable measurement of a single physiological parameter. To provide just one example, two separate patient monitors may be capable of measuring heart rate, such as an ECG device and a pulse oximeter, and the devices may have respective workflows allowing communication of information between the devices to allocate, or divide, monitoring tasks so that redundant measurements of the same physiological parameter are not made. Alternatively, the work flows may operate to provide redundant measurements, and then to determine which one provides the most reliable heart rate value. The most reliable heart rate value may then be provided as the heart rate output of the monitoring system as a whole. To provide another example, a monitoring device may have an available workflow with video camera and/or an audio communication device that activates the video or audio communication when a physiological parameter exceeds an alarm condition so that a clinician can remotely view and/or contact a patient. Corresponding device workflows may provide such imaging and/or communication capabilities. Other examples demonstrate opportunities to reduce the impact of artifacts on measurements. If a device measuring blood pressure (e.g., NIBP device) and a pulse oximeter (SpO2) are on the same arm, the inflation of the cuff will interrupt the SpO2 creating an alarm. A corresponding device workflows between the NIBP device and the pulse oximeter could entail communication and coordination of measurement times to effectuate, for example, temporary suspension of the SpO2 alarm during cuff inflation to prevent a false alarm from occurring. In a similar manner, the use of an airway suctioning device during an automatic NIBP cuff measurement will create artifacts that prevent a successful measurement. If the NIBP device is aware that suctioning, or a similar intervention, is occurring it could delay the inflation of the cuff until the intervention was completed. Thus, corresponding device workflows between the airway suctioning device and the NIBP device could coordinate such a measurement delay.

Once corresponding workflows are identified, each device executes its respective software instructions associated with the respective identified workflow. The devices 3a, 3b, 30 communicate with one another via the established direct communication channel in order to exchange information as needed by the workflow. As part of establishing the workflows to be carried out by the respective devices 3a, 3b, 30, the respective workflow control modules 5a, 5b, 5c determine termination conditions for the workflows being carried out by the respective devices. The termination conditions could be time-based, such as to carry out the workflow for a particular period of time, or they may be event-triggered to cease the workflow upon detection or completion of a specified event. Exemplary event triggers may include, for example, detection of a threshold physiological parameter value, detection of an alarm event, detection of an error or a failure of a respective device 3a, 3b, 30, or a determination that the compatible companion device is no longer detected or is no longer carrying out its corresponding workflow. Once the termination condition is reached, the respective device 3a, 3b, 30 stops carrying out its device workflow and/or terminates the direct communication channel with the compatible device 3a, 3b, 30.

Figure 2:
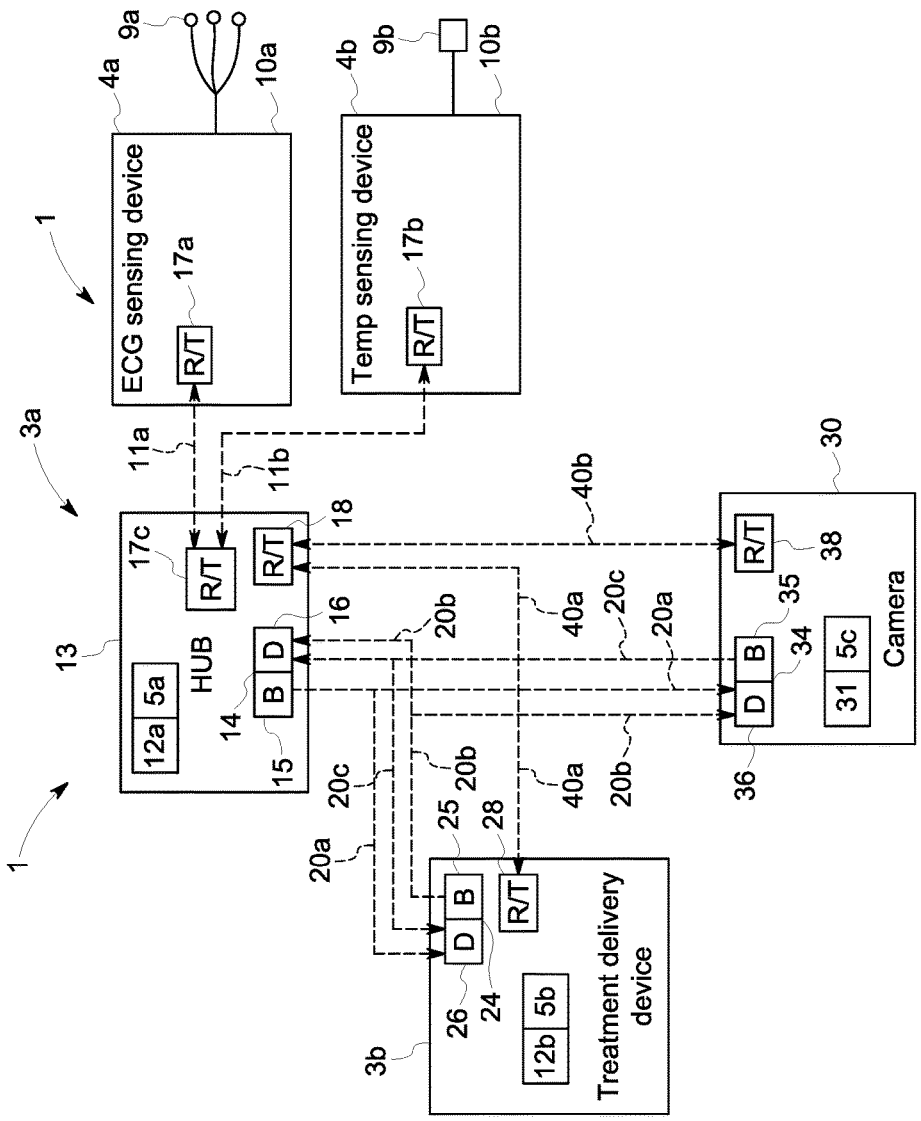
FIG. 2 is a schematic diagram of a different embodiment of a medical device system according to the present disclosure.

FIG. 2 depicts another embodiment of a medical device system 1. In the depicted embodiment, the first medical device 3a includes a multi-parameter wireless patient monitor, and the second medical device 3b is a treatment delivery device. The multi-parameter wireless patient monitor 3a includes two sensing devices 4a and 4b, with the first sensing device 4a being an ECG sensing device and the second sensing device 4b being a temperature sensing device. Each of the sensing devices 4a and 4b measures a physiological parameter from the patient (i.e. cardiac potentials and temperature, respectively) and communicates measurement information to the hub 13. Specifically, each sensing device 4a, 4b has a receiver/transmitter 17a, 17b that communicates with a receiver/transmitter 17c in the hub 13 via wireless communication links 11a, 11b. The hub 13 contains the proximity communication system 14 that communicates with the other devices in the system 1. Likewise, the hub 13 includes the workflow control module 5 and the direct communication receiver/transmitter 18. The hub 13 may control workflows involving the sensing devices 4a, 4b and communicates control instructions and receives physiological parameter data accordingly. In other embodiments, the sensing device 4a, 4b may be more independent, simply utilizing the hub as a communication portal and/or data storage device. In still other embodiments of the system 1, the hub may be eliminated and each sensing device 4a, 4b may be a separate patient monitor medical device 3, each containing their own proximity communication systems and operating as independent and self-sufficient medical devices 3 within the system 1.

In the embodiment depicted in FIG. 2, the sensing devices 4a, 4b each measure different physiological parameter data from the patient. However, a person having ordinary skill in the art will understand in view of this disclosure that the wireless patient monitor system 3a is merely provided as an exemplary patient monitor, and that the disclosed system and method may utilize any type of patient monitor or other medical device, whether connected to the patient via wired or wireless means. Likewise, the monitoring system may include any number of sensing devices 4 and/or separate patient monitors measuring any number of physiological parameters, such as including a non-invasive blood pressure (NIBP) monitor utilizing a blood pressure cuff, a peripheral oxygen saturation ($SpO_2$) monitor having a pulse oximetry sensor (such as configured for placement on a patient's fingertip), an electroencephalograph (EEG) monitor utilizing scalp electrodes, an ultrasound device (such as monitoring perfusion) using an ultrasound transducer, and ECG monitor and/or a temperature monitor as depicted, etc.

In the depicted example, the sensing devices 4a, 4b include one or more sensors 9a, 9b taking physiological parameter measurements. Specifically, each sensing device 4a, 4b includes a data acquisition device 10a, 10b that receives the physiological parameter measurements from the respective sensor 9a, 9b and transmits a parameter dataset based on those measurements to the hub device 13 via communication links 11a and 11b. The sensors 9a, 9b may be any sensors, leads, or other devices available in the art for sensing or detecting physiological information on the patient, which may include electrodes, leadwires, pressure sensors, flow sensors, temperature sensors, blood pressure cuffs, pulse oximetry sensors, ultrasound emitters/transducers, or the like. In the depicted embodiment, the first sensing device 4a is an ECG sensing device having sensors 9a that are ECG electrodes. The second sensing device 4b is a temperature sensing device with sensor 9b being a temperature sensor for measuring a temperature of the patient.

The data acquisition device 10a, 10b of each exemplary sensing device 4a, 4b may include an analog-to-digital (A/D) converter, which may be any device or logic set capable of digitizing analog physiological signals recorded by the associated sensor 9a, 9b. For example, the A/D converter may be an Analog Front End (AFE) device. Each data acquisition device 10a, 10b may further include a processor that receives the digital physiological data from the A/D converter and creates physiological parameter data for transmission to the hub device 13 and/or directly to other devices 3, 30 within the system 1 (depending on the system configuration). Each data acquisition device 10a, 10b may be configured differently depending on the type and function of the respective sensing device 4a, 4b, and may be configured to perform various signal processing functions and/or sensor control functions to provide just a few examples, the ECG sensing device 4a may be configured to filter the digitized signal from the ECG sensors 9a to remove artifact and/or to perform various calculations and determinations based on the recorded cardiac data, such as heart rate, QRS interval, ST segment/interval, etc.

As described above, the sensing devices 4a, 4b may be networked to a central hub or a primary sensing device that collects all patient data, regulates the various sensing devices, and/or monitors an overall patient condition. In certain embodiments having a hub 13, the hub 13 may communicate with a central network for the medical care facility, such as a host network. However, as described above, other embodiments may not have any hub 13 and sensing device 4a, 4b may be a separate patient monitor that communicates within the system 1 and with a host network for the healthcare facility.

In the depicted embodiment of FIG. 2, the system 1 includes a medical device 3b being a treatment delivery device. A treatment delivery device delivers treatment to the patient, such as medication, anesthesia, respiratory therapy, physical or other therapy, temperature regulation, etc. Non-limiting examples of treatment delivery devices and systems include anesthesia delivery devices, infusion pumps of various sorts, ventilators, respirators, and blood glucose maintenance systems. In the depicted example, the treatment delivery device 3b includes the proximity communication system 24 that emits a beacon signal 20b that is received by the other devices 3a, 30 in the system 1. Thus, compatibility assessments happen between each of the devices in the system, and direct communication channels 40a and 40b are established based thereon. In the depicted example, no communication link is established between the treatment delivery device 3b and the camera 30 because, for example, the respective devices were incompatible or because there were no corresponding workflows between the two devices.

In FIG. 2, the camera 30 has a proximity communication system 34 having both a proximity beacon 35 and a proximity detector 36. The proximity beacon 35 emits beacon signal 20c that is received at the proximity communication systems 14 and 24. The patient monitor 3a establishes two different direct communication channels 40a and 40b with the treatment delivery device 3b and the camera 30, respectively. Thereby, workflows can be carried out between the patient monitor 3a and each of the other devices 3b and 30. For example, the treatment delivery device 3b may be controlled based on physiological parameters of the patient measured by the patient monitor 3a. In an example where the treatment delivery device 3b is a drug delivery device, drug delivery can be controlled based on cardiac data measured by the ECG sensing device 4a. For instance, medication may be delivered to the patient based on the patient's heart rate, for example. Similarly, a workflow may be carried out between the treatment delivery device 3b and the patient monitor 3a to adjust the alarm threshold for the ECG sensing device 4a based on the drug delivery to the patient. Thereby, false alarms, such as due to an expected medication-induced heart rate change can be avoided. In other embodiments, the treatment delivery device 3b may be a temperature regulation device, such as a warming bed or mattress, a heating blanket, a heating lamp, a cooling blanket or cooling pad. In such embodiments, the temperature regulating treatment delivery device 3b may be controlled based on temperature measurements from the temperature sensing device 4b, which are provided according to a workflow utilizing the direct communication channel 40a.

The medical devices 3 and other devices 30 shown and described in FIGS. 1 and 2 are for purposes of providing explanatory examples and are not limiting. Generally, the disclosed system 1 may employ any number of medical or patient care devices capable of the proximity detection and compatibility analysis, as well as the exchange of workflow information and execution of workflows as described herein.

Figure 3:
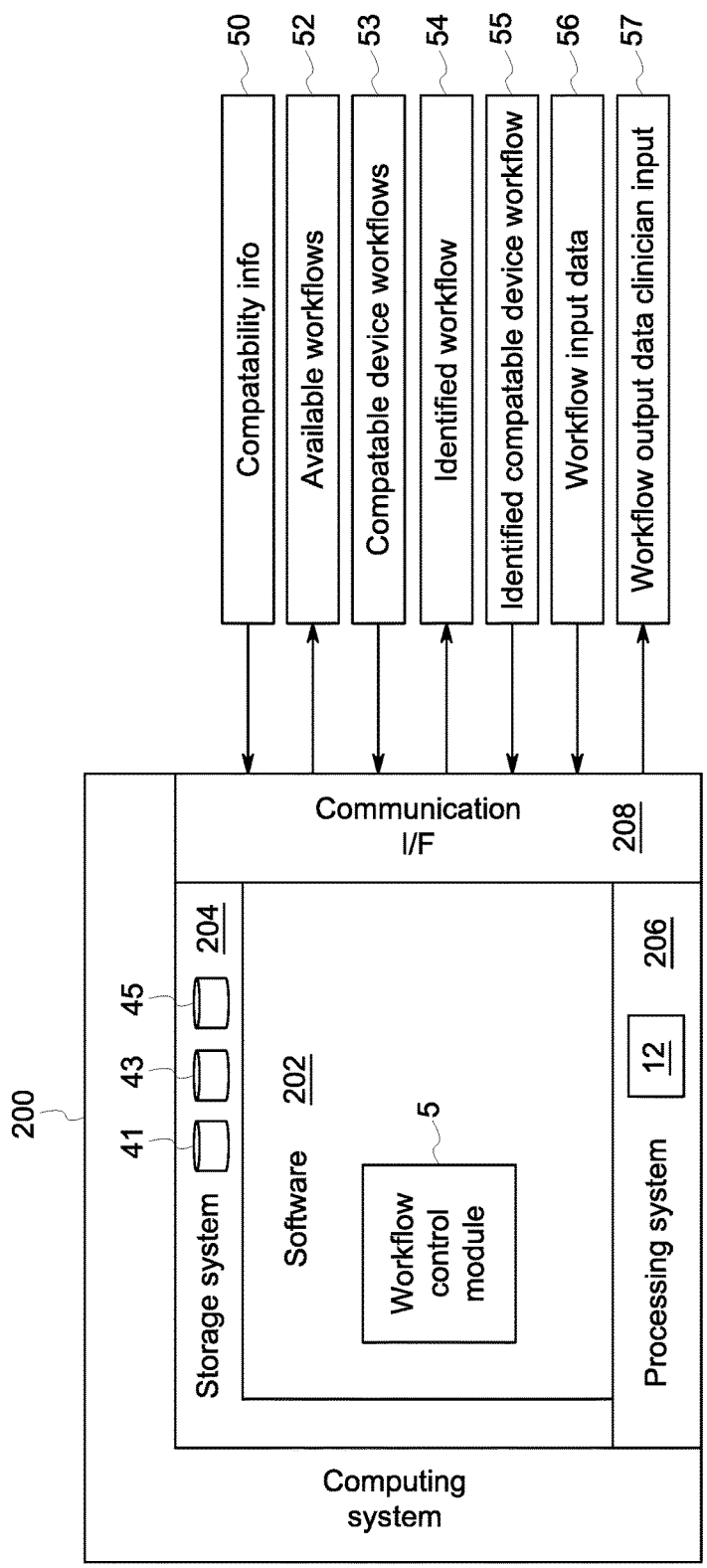
FIG. 3 is a schematic diagram of a computing system containing a work flow control module to be incorporated in a medical device or other device within the medical device system.

FIG. 3 provides a schematic diagram of a computing system 200 incorporated in a device operating as part of the system 1. The computing system 200 includes a processing system 206, storage system 204, software 202, and a communication interface 208. The processing system 206 loads and executes software 202 from the storage system 204, including the workflow control module 5, which is an application within the software 202. The workflow control module 5 comprises computer-readable instructions that, when executed by the computing system 200 (including the processing system 206), direct the processing system 206 to operate as described in herein in further detail.

Although the computing system 200 as depicted in FIG. 3 includes one software 202 encapsulating one workflow control module 5, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 12, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 includes the compatibility database 41, the workflow database 43, and the workflow log 45. In other examples, one or more of the databases 41, 43, 45 may be stored remotely and accessible to the computing system 200 of the respective medical device 3 (or other device in the system 1), such as via wireless communication means. The storage system 204 may comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the databases 41, 43, 45, one or more of which may likewise be each stored on separate storage devices. Likewise, the databases 41, 43, 45 may be stored, distributed, and/or implemented across one or more storage media or group of storage medias. Similarly, the databases 41, 43, 45, may encompass multiple different sub-databases at different storage locations and/or containing different information which may be stored in different formats.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as with the proximity communication system 14, 24, 34 of the respective device 3a, 3b, 30 to facilitate receipt of compatibility information from other devices in the system 1. The communication interface 208 also facilitates transmission and receipt of information via the direct communication receiver/transmitter 18, 28, 38 of the respective device 3a, 3b, 30. For example, during the workflow assessment process, available workflows 52 for the respective device 3a, 3b, 30 are transmitted and available workflows for the compatible devices in the system 1 (i.e., compatible device workflows 53) are received via the direct communication channel 40a, 40b. Corresponding workflows may be identified between an identified workflow 54 of the device 3 (e.g., the patient monitor 3a) and the identified compatible device workflow 55 of the compatible device (e.g., the treatment delivery device 3b and the video camera 30). Then workflow input data 56 is received from the compatible device per the implemented workflows. Likewise, the respective device outputs data as part of the execution of its identified workflow 54 (i.e., workflow output data 57). Both the workflow input data 56 and the workflow output data 57 is communicated via the direct communication channels 40a, 40b established between the respective devices executing the workflow.

Figure 4:
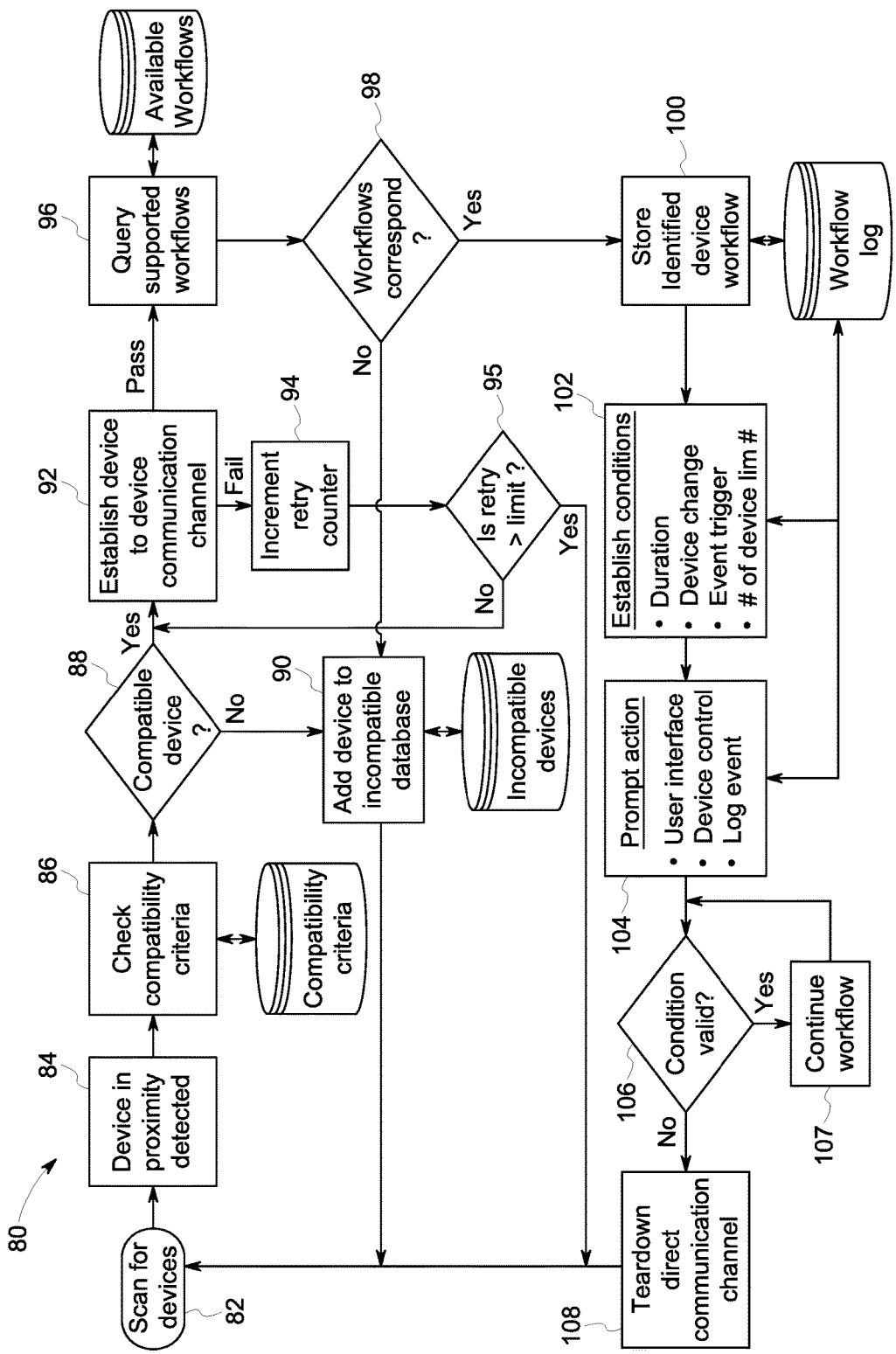
FIG. 4 is an exemplary flowchart depicting one embodiment of a method of controlling a system of medical devices connected to a patient.

FIG. 4 depicts one embodiment of a method 80 of controlling a system 1 of medical devices connected to a patient. The depicted steps exemplify actions by one medical device in the system 1, and each device in the system 1 may execute the same or similar steps in parallel to cooperate in identifying and carrying out corresponding workflows. Step 82 is executed to scan for devices. Namely, the device proximity detector 16, 26, 36 may scan to detect beacon signals 20 from proximity beacons 15, 25, 35 in other devices 3a, 3b, 30 that could be part of the system 1. A beacon signal 20 is detected at step 84, indicating that a potentially-compatible device is within a predetermined proximity range of that searching device. In various embodiments, the predetermined proximity range may be set to various distances, which is dependent on the particular proximity-based technology and the configuration thereof. Different physiological measurements and workflows may require different ranges of detection, such as based on how far apart the devices are likely to be placed on or near the patient. Other factors, such as likely environmental interference and battery concerns may also play a role in establishing the predetermined proximity range for transmission of the beacon signal 20 by the proximity beacon 15, 25, 35.

The compatibility criteria is then checked at step 86, such as by comparing the received compatibility information to compatibility criteria stored in a compatibility database 41. As described above, the compatibility database 41 may be stored locally within the respective device 3a, 3b, 30, or may be stored remotely, such as on a host network of the healthcare facility or a remote storage facility. Step 88 assesses whether compatibility exists with the discovered device. If not, then the compatibility information from the incompatible device is added to a list of incompatible devices at step 90, such as a database containing compatibility information for already-discovered incompatible devices. Such a list of incompatible devices may be part of the check for compatibility criteria at step 86, such as verifying that the compatibility information does not match any already-discovered incompatible device.

If compatibility is established at step 88, then step 91 is executed to establish a direct communication channel 40a, 40b, i.e., a device-to-device communication channel, between the compatible devices. A limit may be established on the number of attempts for establishing a communication channel between the two devices. If an attempt to establish the direct communication channel 40a, 40b fails, then an increment counter is increased at step 94 and compared to the re-try limit at step 95. Repeated attempts are made to establish the direct communication channel until the limit is reached at step 95, at which point the attempt to establish the direct communication channel is terminated and no workflow comparison is made.

Once the direct communication channel 40a, 40b is established, the devices exchange information regarding each of their available workflows. The workflow control module 5 may access a workflow database containing available workflows that can be performed by the respective device 3a, 3b, 30. The workflow database 43 may be contained locally in the respective device 3a, 3b, 30 or remotely, as described above. A device communicates its available workflows 52 to the compatible device and receives compatible device workflows 53 from the compatible device. A comparison is made to see if any of the compatible device workflows 53 correspond with the devices available workflows 52. To that end, step 98 is conducted to determine whether any corresponding workflows exist between the respective devices' available workflows. If no corresponding workflows exist, then the device, such as identified by its compatibility information, may be added to the incompatible list (such as stored in the compatibility database). Thereby, the respective workflow control module 5 can avoid repeated workflow assessments with the same device.

Once a corresponding device workflow is discovered (e.g. a treatment delivery device 3b identifies a corresponding monitor workflow if the patient monitor 3a to its available treatment delivery workflow), then the identified device workflows are stored in a workflow log at step 100. As described above, the workflow log 45 documents execution of the workflows with other devices, including changes that may be made to the operation of a particular device 3a, 3b, 30 during the joint action between the devices executing corresponding workflows. Thus, at step 100, the identified device workflows are stored (such as by workflow identification numbers), along with timestamps marking the initiation of the workflow. Additionally, timestamps may be logged to show the time that the direct communication channel was established at step 92. Other information may also be logged during execution of the workflow, such as values received from the compatible device and actions taken as a result of the received values. Thereby, a detailed patient care record is automatically established.

Conditions of the workflow are established and logged at step 102, such as termination conditions upon which the workflow between the two devices will be stopped. Termination conditions may be, for example, a passing of a particular duration of time or a detection of a particular event, such as completion of a therapy or treatment action or a desired physiological parameter value. Multiple termination conditions may be established, any of which may trigger termination of the workflow. Additional exemplary termination conditions discontinued detection of the beacon signal 20 from the proximity beacon 15 of the other device, which could result from removal of that device from the system 1 or malfunctioning of that device. Termination conditions may also relate to limiting the number of other devices with which a particular device is paired. Thus, if a device limit is reached, then an assessment may be made to prioritize certain workflows over others, and to terminate the lower priority workflows. For example, the workflow database 43 may have information ranking the available workflows in order of priority, such as in order of criticality for patient care.

The device then executes its workflow at step 104 and logs the steps executed in the workflow log 45. In certain embodiments, initiation of the workflow may require input from a clinician. For example, instructions may be executed as part of step 104 to provide a prompt on the user interface asking a clinician if the workflow should be initiated, such as to perform combined physiological measurements, adjust alarm limits based on drug information, or control a non-medical device in the system (which is referencing a few of the examples provided above). Step 106 is executed to make sure that the termination conditions have not been reached. Execution of the respective workflows is continued at step 107 until a termination condition is reached. At that point, the direct communication channel 40a, 40b between the devices is terminated at step 108.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:
1. A medical device system comprising:
    a first patient monitor configured to measure a physiological parameter from a patient, the first patient monitor including a proximity beacon, wherein the proximity beacon communicates compatibility information;
    a medical device associated with the patient, the medical device including:

a device proximity detector configured to detect the proximity beacon when the first patient monitor is within a predetermined proximity range of the medical device;

a processor;

a device workflow control module executable on the processor to:

receive, via the device proximity detector, the compatibility information from the first patient monitor;

determine based on the compatibility information whether the first patient monitor is a compatible device with the medical device;

if the first patient monitor is a compatible device, establish a direct communication channel with the first patient monitor;

identify one of a set of available device workflows executable by the medical device that corresponds with one of a set of available monitor workflows executable by the first patient monitor;

determine at least one termination condition for the identified device workflow; and communicate with the first patient monitor via the direct communication channel so as to execute the identified device workflow until the termination condition is reached.

2. The system of claim 1, wherein the compatibility information includes at least one of a medical device type, a make of the medical device, a model of the medical device, a serial number of the medical device, and a patient identifier for the patient, and the determination of compatibility includes determining whether the compatibility information matches compatibility criteria stored in a compatibility database.

3. The system of claim 1, wherein the first patient monitor further comprises a device proximity detector and the medical device further comprises a proximity beacon communicating compatibility information for the medical device, processor and a monitor workflow control module executable on the processor to:

receive the compatibility information from the medical device;

determine based on the compatibility information whether the medical device is a compatible device with the first patient monitor;

if the first patient monitor is a compatible device, establish the direct communication channel with the medical device;

identify one of the set of available monitor workflows that corresponds with one of the set of available device workflows executable by the medical device;

determine at least one termination condition for the identified monitor workflow; and communicate with the medical device via the direct communication channel so as to execute the identified monitor workflow until the termination condition is reached.

4. The system of claim 3, wherein the medical device is a treatment delivery device configured to administer treatment to the patient and the identified device workflow is a treatment delivery workflow for controlling administration of the treatment, and wherein the first patient monitor is at least one of an ECG monitor, an SPO2 monitor, an NIBP monitor, a temperature monitor, and an EEG monitor.

5. The system of claim 4, further comprising a workflow log accessible by the first patient monitor, and wherein the monitor workflow control module is further executable on the processor to, upon identifying the identified monitor workflow that corresponds with the device workflow, log initiation of the identified monitor workflow in the workflow log.

6. The system of claim 5, wherein the treatment delivery device is a drug delivery device, and wherein the monitor workflow control module executing the identified monitor workflow is further executable on the processor to:

receive a drug delivery amount from the drug delivery device via the direct communication channel;

adjust an alarm threshold for the first patient monitor based on the drug delivery amount; and log the alarm threshold adjustment and the drug delivery amount in the workflow log.

7. The system of claim 4, further comprising a workflow log accessible by the treatment delivery device, and the wherein the device workflow control module is further executable on the processor to, upon identifying the treatment delivery workflow that corresponds with the monitor workflow, log initiation of the identified treatment delivery workflow in a workflow log.

8. The system of claim 7, wherein the treatment delivery device is a drug delivery device, and wherein the device workflow control module executing the identified treatment delivery workflow is further executable on the processor to:

receive physiological parameter data from the first patient monitor via the direct communication channel;

adjust drug delivery based on the physiological parameter data; and log the drug delivery adjustment in the workflow log.

9. The system of claim 3, wherein the treatment delivery device is a temperature regulation device and the first patient monitor measures a body temperature of the patient, and wherein the device workflow control module executing the treatment delivery workflow is further executable on the processor to:

receive temperature data from the first patient monitor; and adjust the temperature regulation device based on the temperature data.

10. The system of claim 3, further comprising a video camera, wherein the monitor workflow control module executing the identified monitor workflow is further executable on the processor to:

detect with the device proximity detector in the medical device that the video camera is within a proximity range of the medical device;

establish a second direct communication channel with the video camera; and upon detection of an alarm condition, communicate an instruction to the video camera via the second direct communication channel to video record the patient.

11. The system of claim 1, wherein the medical device is a second patient monitor and the device workflow is a second monitor workflow, wherein the device workflow control module executing the second monitor workflow is further executable on the processor to:

adjust at least one of a physiological parameter measured, a measurement interval, and an alarm threshold for the second patient monitor to allocate physiological parameter measurements between the first patient monitor and the second patient monitor.

12. The system of claim 1, the medical device further comprising a compatibility database accessible by the medical device containing compatibility information for already-identified compatible and/or incompatible devices; and wherein the device workflow control module is further configured to if the first patient monitor is not a compatible device, add the compatibility information received from the first patient monitor to the compatibility database as an already-identified incompatible device.

13. The system of claim 1, wherein the proximity detector is one of an NFC device, an RFID device, or a Bluetooth device, and wherein the direct communication channel is one of an Ethernet communication channel, a Wi-Fi communication channel, a WMTS communication channel, or a Bluetooth communication channel.

14. The system of claim 1, wherein the termination condition includes discontinued detection of the first patient monitor within the proximity range by the device proximity detector in the medical device.

15. A method of controlling a system of medical devices connected to a patient, the method comprising:
   in a first patient monitor configured to monitor a physiological parameter of the patient, detecting with a device proximity detector that a medical device is within a proximity range of the first patient monitor;
   receiving compatibility information from the medical device;
   determining, based on the compatibility information, whether the medical device is compatible with the first patient monitor;
   if the medical device is compatible, establishing a direct communication channel with the patient monitor;
   communicating with the medical device via the direct communication channel to identify one of a set of available monitor workflows executable by the patient monitor that corresponds with one of a set of available device workflows executable by the medical device;
   determining at least one termination condition for the identified monitor workflow; and
   communicating with the medical device via the direct communication channel so as to execute the identified monitor workflow until the termination condition is reached.

16. The method of claim 15, wherein the medical device is a treatment delivery device configured to administer treatment to the patient, and further comprising:
   receiving treatment delivery information from the treatment delivery device; and
   adjusting at least one of a physiological parameter measured, a measurement interval, and an alarm threshold for the patient monitor based on the treatment delivery information.

17. The method of claim 16, further comprising:
   at the first patient monitor, transmitting physiological parameter data to a drug delivery device via the direct communication channel;
   at the drug delivery device:
     receiving physiological parameter data from the patient monitor; and
     adjusting drug delivery to the patient based on the physiological parameter data.

18. The method of claim 17, wherein the drug delivery device delivers medication and the at least one termination condition includes receipt of physiological parameter data indicating achievement of a desired effect of the medication;
   wherein the method further includes, at the drug delivery device:
     controlling delivering the medication to the patient;
     determining that the physiological parameter data indicates achievement of the desired effect of the medication;
     terminating the treatment delivery workflow; and
     logging the termination of the treatment delivery workflow in a workflow log.

19. The method of claim 15, further comprising:
   detecting with the device proximity detector that a video camera is within a proximity range of the first patient monitor;
   establishing a second direct communication channel with the video camera;
   determining that a physiological parameter measured from the patient has crossed an alarm threshold;
   communicating an instruction to the video camera via the second direct communication channel to video record the patient if physiological parameter data crosses the alarm threshold.

20. The method of claim 15, wherein the compatibility information includes at least one of a medical device type, a make of the medical device, a model of the medical device, a serial number of the medical device, and a patient identifier for the patient, and the determination of compatibility includes determining whether the compatibility information matches compatibility criteria stored in a compatibility database.

21. The method of claim 15, wherein the medical device is a second patient monitor monitoring a different physiological parameter than the first patient monitor, the method further comprising:
   at the first patient monitor, receiving physiological parameter information from the second patient monitor; and
   adjusting at least one of a physiological parameter measured, a measurement interval, and an alarm threshold for the first patient monitor based on the physiological parameter information from the second patient monitor.

* * * * *